US012678565B2

(12) United States Patent
Sim et al.

(10) Patent No.: US 12,678,565 B2
(45) Date of Patent: Jul. 14, 2026

(54) AMPOULE-FIXING HOLDER FOR INTRAOSSEOUS ANESTHETIC SOLUTION INJECTION DEVICE AND ANESTHETIC SOLUTION INJECTION DEVICE INCLUDING THE SAME

(71) Applicant: DENTIS CO., LTD., Daegu (KR)

(72) Inventors: Gi Bong Sim, Daegu (KR); Jun Oh Kim, Daegu (KR); Si Mok Kim, Daegu (KR); Hwal Kim, Daegu (KR); Ji Hong So, Gyeongsangbuk-do (KR); Gyeong Seob Kim, Daegu (KR)

(73) Assignee: DENTIS CO., LTD., Daegu (KR)

( * ) Notice: Subject to any disclaimer, the term of this patent is extended or adjusted under 35 U.S.C. 154(b) by 502 days.

(21) Appl. No.: 18/341,267

(22) Filed: Jun. 26, 2023

(65) Prior Publication Data

US 2024/0148976 A1     May 9, 2024

(30) Foreign Application Priority Data

Nov. 3, 2022     (KR) ........................ 10-2022-0144870

(51) Int. Cl.
*A61M 5/24* (2006.01)
*A61M 5/315* (2006.01)

(52) U.S. Cl.
CPC .......... *A61M 5/24* (2013.01); *A61M 5/31576* (2013.01); *A61M 2205/50* (2013.01); *A61M 2205/8206* (2013.01)

(58) Field of Classification Search
CPC ............ A61B 17/3472; A61M 5/2422; A61M 2005/2407; A61M 2005/2433; A61M 2005/2437; A61M 2005/244; A61M 2005/3289; A61M 2210/02
See application file for complete search history.

(56) References Cited

U.S. PATENT DOCUMENTS

| | | | | |
|---|---|---|---|---|
| 4,787,893 A | * | 11/1988 | Villette | A61C 19/08 604/188 |
| 5,927,976 A | * | 7/1999 | Wu | A61C 19/08 433/80 |
| 6,183,442 B1 | * | 2/2001 | Athanasiou | A61M 5/20 604/154 |
| 2005/0171504 A1 | * | 8/2005 | Miller | A61B 17/1671 604/506 |
| 2005/0261693 A1 | * | 11/2005 | Miller | A61B 17/3472 606/80 |
| 2010/0049126 A1 | * | 2/2010 | Bronfeld | A61B 5/150114 604/113 |

(Continued)

*Primary Examiner* — Kami A Bosworth
(74) *Attorney, Agent, or Firm* — Mendelsohn Dunleavy, P.C.

(57) ABSTRACT

Disclosed are an ampoule-fixing holder for an intraosseous anesthetic solution injection device and an anesthetic solution injection device including the same. The ampoule-fixing holder includes a cylindrical holder body including an open portion formed at the rear end thereof to allow an ampoule containing an anesthetic solution to be inserted thereinto or removed therefrom, a head configured to enable mounting of an injection needle to the front end of the holder body, a rotary body disposed between the head and the holder body to withstand rotational force and an axial load, and a fixing member configured to firmly hold the ampoule inserted into the holder body to effectively transmit rotational force to the ampoule.

8 Claims, 6 Drawing Sheets

(56)         References Cited

U.S. PATENT DOCUMENTS

| 2010/0168638 A1* | 7/2010 | Korogi | A61M 35/006 |
| | | | 401/133 |
| 2011/0152780 A1* | 6/2011 | Villette | B65D 1/0223 |
| | | | 604/187 |
| 2011/0152793 A1* | 6/2011 | Villette | A61M 5/482 |
| | | | 604/272 |
| 2013/0103048 A1* | 4/2013 | Burg | A61B 90/11 |
| | | | 606/129 |
| 2016/0228648 A1* | 8/2016 | Goraltchouk | A61M 5/24 |
| 2018/0256209 A1* | 9/2018 | Muse | A61B 17/3472 |
| 2024/0399065 A1* | 12/2024 | Dunne | A61M 5/24 |

* cited by examiner

AMPOULE-FIXING HOLDER FOR INTRAOSSEOUS ANESTHETIC SOLUTION INJECTION DEVICE AND ANESTHETIC SOLUTION INJECTION DEVICE INCLUDING THE SAME

CROSS-REFERENCE TO RELATED APPLICATION

This application claims priority from Korean Patent Application No. 10-2022-0144870, filed on Nov. 3, 2022, in the Korean Intellectual Property Office, the disclosure of which is incorporated herein by reference in its entirety.

BACKGROUND OF THE INVENTION

Field of the Invention

The present invention relates to an ampoule-fixing holder for an intraosseous anesthetic solution injection device and an anesthetic solution injection device including the same, and more particularly to an ampoule-fixing holder for an intraosseous anesthetic solution injection device, which is capable of effectively transmitting power of a motor to an ampoule without rotational slippage by stably fixing the ampoule and capable of preventing variation in fixing force caused by variation in outer diameter of ampoules, and an anesthetic solution injection device including the same.

Description of the Related Art

In general, dental treatment, such as nerve treatment, tooth extraction, or implantation, requires intraosseous dental anesthesia. In this case, an anesthetic solution is injected into a desired area through cortical bone of the jaw. In order to inject an anesthetic solution into a certain area through cortical bone, it is necessary to rotate an injection needle so that the injection needle penetrates the cortical bone. An anesthetic solution injection device having such a rotary injection needle requires an ampoule holder to hold an ampoule.

As conventional art related thereto, U.S. Pat. No. 9,028, 455B2 discloses a cylindrical holder for housing a pharmaceutical product container in a handpiece of a surgical instrument for perforating dense tissue of a human or animal body and injecting a pharmaceutical product into the tissue. The cylindrical holder according to the conventional art has a plurality of cut-outs formed in the outer circumferential surface thereof and first and second bridges formed between the cut-outs. The bridges resiliently deflect toward the central axis of the holder so that the holder has a smaller inner diameter at the bridges than at the two ends of the holder.

However, the above conventional art is difficult to manufacture because the sizes of the inner and outer diameters of the holder are not uniform due to the bridges and the bridges deflect inwardly inside the holder. Therefore, the conventional art has problems of long manufacturing time and high manufacturing cost.

Further, according to the conventional art, because only a portion of the holder that has a relatively small inner diameter due to the bridges fixes an ampoule, a force of fixing the ampoule may not be sufficient depending on the type of ampoule, particularly the size of the outer diameter of an ampoule or the properties of the surface of an ampoule.

Furthermore, according to the conventional art, the holder may be deformed over time due to the material characteristics thereof, and thus a force of fixing an ampoule using the bridges may become weak over time.

SUMMARY OF THE INVENTION

The present invention has been made to solve the above problems, and it is an object of the present invention to provide an ampoule-fixing holder for an intraosseous anesthetic solution injection device, which is capable of effectively transmitting power of a motor to an ampoule without rotational slippage by stably fixing the ampoule and capable of reducing manufacturing time and cost, and an anesthetic solution injection device including the same.

In addition, it is another object of the present invention to provide an ampoule-fixing holder for an intraosseous anesthetic solution injection device, which is capable of preventing variation in fixing force caused by variation in outer diameter of ampoules and capable of preventing reduction in fixing force due to deformation of the ampoule-fixing holder over time, and an anesthetic solution injection device including the same.

In accordance with an aspect of the present invention, the above and other objects can be accomplished by the provision of an ampoule-fixing holder for an intraosseous anesthetic solution injection device, the ampoule-fixing holder including a cylindrical holder body including an open portion formed at the rear end thereof to allow an ampoule containing an anesthetic solution to be inserted thereinto or removed therefrom, a head configured to enable mounting of an injection needle to the front end of the holder body, a rotary body disposed between the head and the holder body to withstand rotational force and an axial load, and a fixing member configured to firmly hold the ampoule inserted into the holder body to effectively transmit rotational force to the ampoule.

The fixing member may be implemented as an elastic rubber ring configured to be first fitted on the open portion of the holder body and then shifted to be mounted on the outer circumferential surface of the holder body. The holder body may include a mounting groove formed in the middle portion thereof to a predetermined depth to allow the elastic rubber ring to be mounted therein and a plurality of slits formed therein in the longitudinal direction of the holder body about the central axis of the holder body. When the elastic rubber ring is fitted on the open portion of the holder body, the holder body may elastically contract in the circumferential direction thereof to allow the elastic rubber ring to be fitted into the mounting groove.

The fixing member may include at least one protruding portion formed on the inner surface thereof so as to come into contact with the surface of the ampoule to transmit rotational force to the ampoule when the holder body is rotated. The mounting groove may include at least one insertion hole formed therein to allow the at least one protruding portion to pass therethrough and to come into contact with the surface of the ampoule.

The at least one protruding portion may include a plurality of protruding portions disposed so as to be spaced apart from each other at regular intervals, and the at least one insertion hole may include a plurality of insertion holes disposed so as to be spaced apart from each other at regular intervals. The plurality of slits and the plurality of insertion holes may alternately be formed in the outer circumferential surface of the holder body.

The holder body may include a first slanted portion and a second slanted portion formed in front of and behind the mounting groove, respectively. Each of the first slanted portion and the second slanted portion may gradually increase in thickness toward the mounting groove so as to have a larger outer diameter than the holder body.

The plurality of slits may be formed in the holder body in the longitudinal direction of the holder body so as to cross the second slanted portion and the mounting groove.

The ampoule-fixing holder may further include a fixing-member holder configured to be fitted on the outer surface of the fixing member in order to hold the fixing member mounted in the mounting groove in the holder body.

The head may be bonded to a front portion of the holder body using an adhesive.

In accordance with another aspect of the present invention, there is provided an anesthetic solution injection device including an ampoule containing an anesthetic solution, the above-described ampoule-fixing holder configured to fix the ampoule, an injection needle mounted to one end of the ampoule-fixing holder, and a handpiece including a pusher inserted into the opposite end of the ampoule-fixing holder to push and fix the ampoule inserted into the ampoule-fixing holder and a spring configured to push the ampoule-fixing holder mounted in the handpiece using resilient force thereof at the opposite end of the ampoule-fixing holder.

The handpiece may include a motor configured to generate pressure to eject the anesthetic solution through the injection needle, a user input unit configured to allow a user to input a command for control of operation of the handpiece, a controller configured to control the motor in response to the command received from the user input unit, and a battery configured to supply power to the user input unit.

BRIEF DESCRIPTION OF THE DRAWINGS

The above and other objects, features, and other advantages of the present invention will be more clearly understood from the following detailed description taken in conjunction with the accompanying drawings, in which.

DETAILED DESCRIPTION OF THE INVENTION

Figure 1:
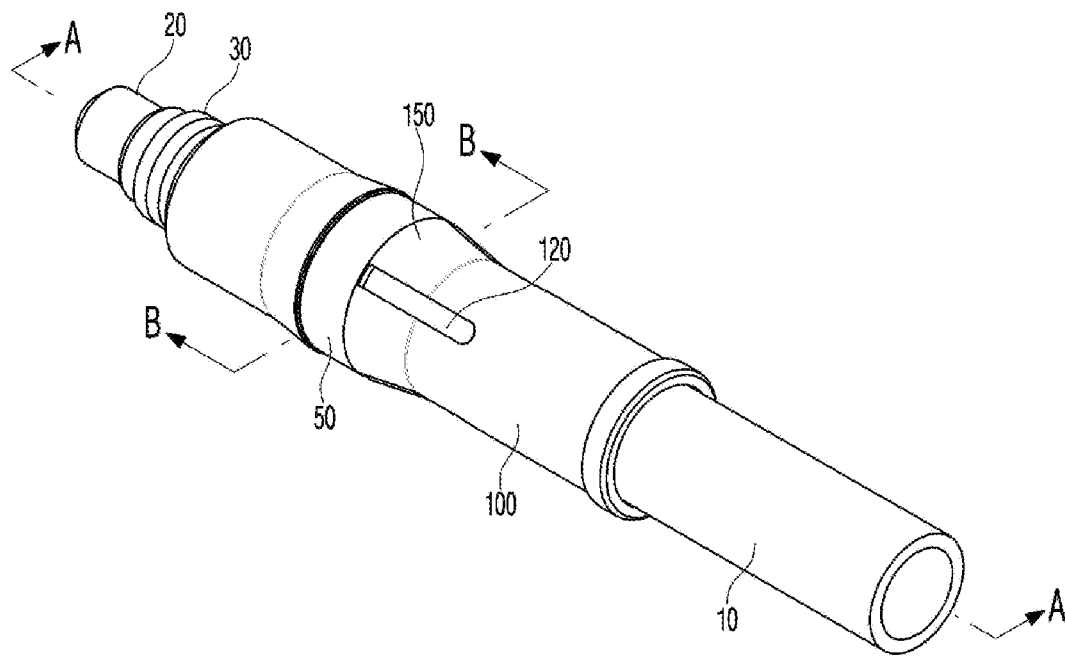
FIG. 1 is an overall perspective view showing an ampoule and an ampoule-fixing holder according to an embodiment of the present invention.

Hereinafter, exemplary embodiments of the present invention will be described in detail with reference to the accompanying drawings. It should be noted that when reference numerals are assigned to the elements of the drawings, the same elements are denoted by the same reference numerals even when they are depicted in different drawings. The configuration and the operation of the present invention illustrated and described in the drawings are described as at least one embodiment, and the technical spirit of the present invention and the core configuration and the operation thereof are not limited thereto.

The present invention relates to an anesthetic solution injection device having a rotary injection needle in order to inject an anesthetic solution into a desired area through cortical bone of the jaw during dental treatment, such as nerve treatment, tooth extraction, or implantation, and more particularly to an ampoule-fixing holder configured to hold an ampoule that rotates together with the injection needle.

Figure 2:
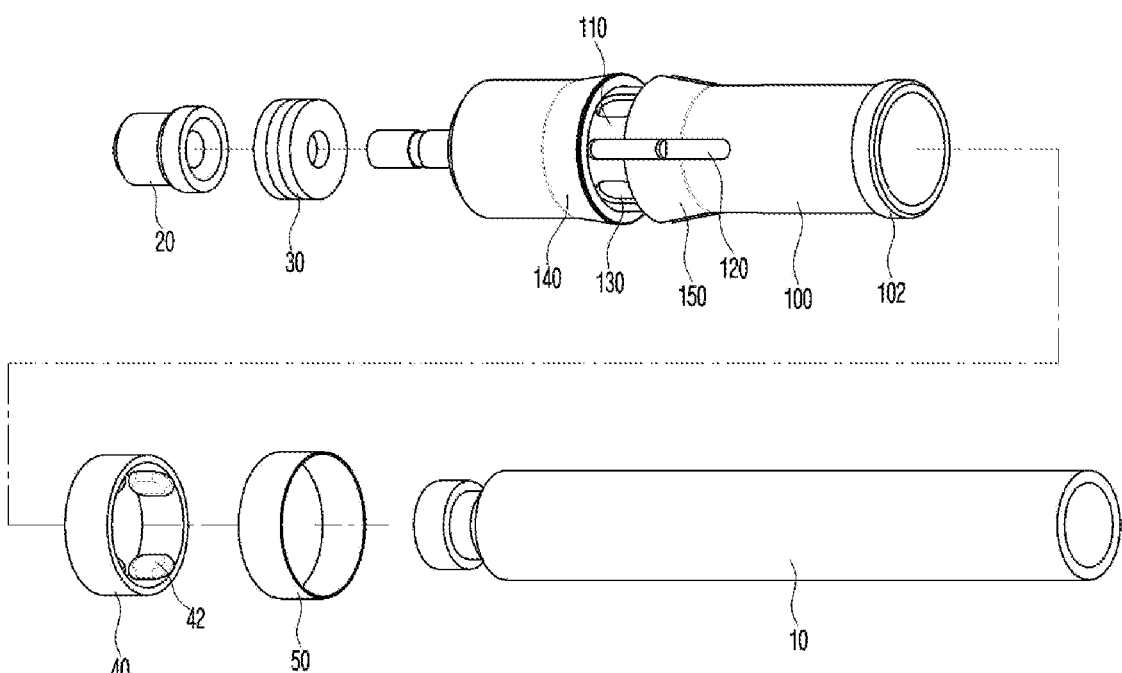
FIG. 2 is an exploded perspective view showing the ampoule and the ampoule-fixing holder according to the embodiment of the present invention.

FIG. 1 is an overall perspective view showing an ampoule and an ampoule-fixing holder according to an embodiment of the present invention, and FIG. 2 is an exploded perspective view showing the ampoule and the ampoule-fixing holder according to the embodiment of the present invention.

As shown in the drawings, the ampoule-fixing holder according to the embodiment of the present invention includes a cylindrical holder body 100 including an open portion 102 formed at the rear end thereof to allow an ampoule 10 containing an anesthetic solution to be inserted thereinto or removed therefrom, a head 20 configured to enable mounting of an injection needle (not shown) to the front end of the holder body 100, a rotary body 30 disposed between the head 20 and the holder body 100 to withstand rotational force and an axial load, and a fixing member 40 configured to firmly hold the ampoule 10 inserted into the holder body 100 to effectively transmit rotational force to the ampoule 10.

The holder body 100 serves to fix the ampoule 10, which is a container containing an anesthetic solution. In order to fix the ampoule 10, the holder body 100 is formed in a cylindrical shape to allow the ampoule 10 to be inserted thereinto.

According to the present invention, the holder body 100 has a cylindrical shape, the inner circumferential surface of which has a uniform inner diameter so that the ampoule 10 is easily inserted thereinto or removed therefrom. The fixing member 40 is fitted on the holder body 100 in order to hold the ampoule 10 inserted into the holder body 100 having a uniform inner diameter.

The holder body 100 is provided at one end thereof, i.e. the front end thereof, with a front portion on which the head 20 and the rotary body 30 are fitted. The head 20 is bonded to the front portion of the holder body 100 using an adhesive.

The head 20 may have a thread formed on the outer surface thereof so that a rotary injection needle is tooth-engaged therewith, whereby the rotary injection needle is firmly coupled to the head 20. Accordingly, the rotary injection needle is prevented from being separated from the head 20 when rotated.

The rotary body 30 is fitted on the front portion of the holder body 100 to withstand rotational force and an axial load of the ampoule-fixing holder. Preferably, the rotary body 30 is implemented as a rotary bearing.

As described above, the present invention is characterized by the fixing member 40 configured to firmly hold the ampoule 10 inserted into the holder body 100 to effectively transmit rotational force to the ampoule 10.

According to the present invention, the fixing member 40 is implemented as an elastic rubber ring, and is first fitted on the open portion 102 formed at the rear end of the holder body 100 and then is shifted to be mounted on the outer circumferential surface of the holder body 100. That is, it is preferable for the fixing member 40 to be made of rubber, which is a material that is elastically stretchable and capable of holding the holder body 100 when mounted on the holder body 100. The fixing member 40 has a ring shape mountable on the outer circumferential surface of the holder body 100.

Figure 3:
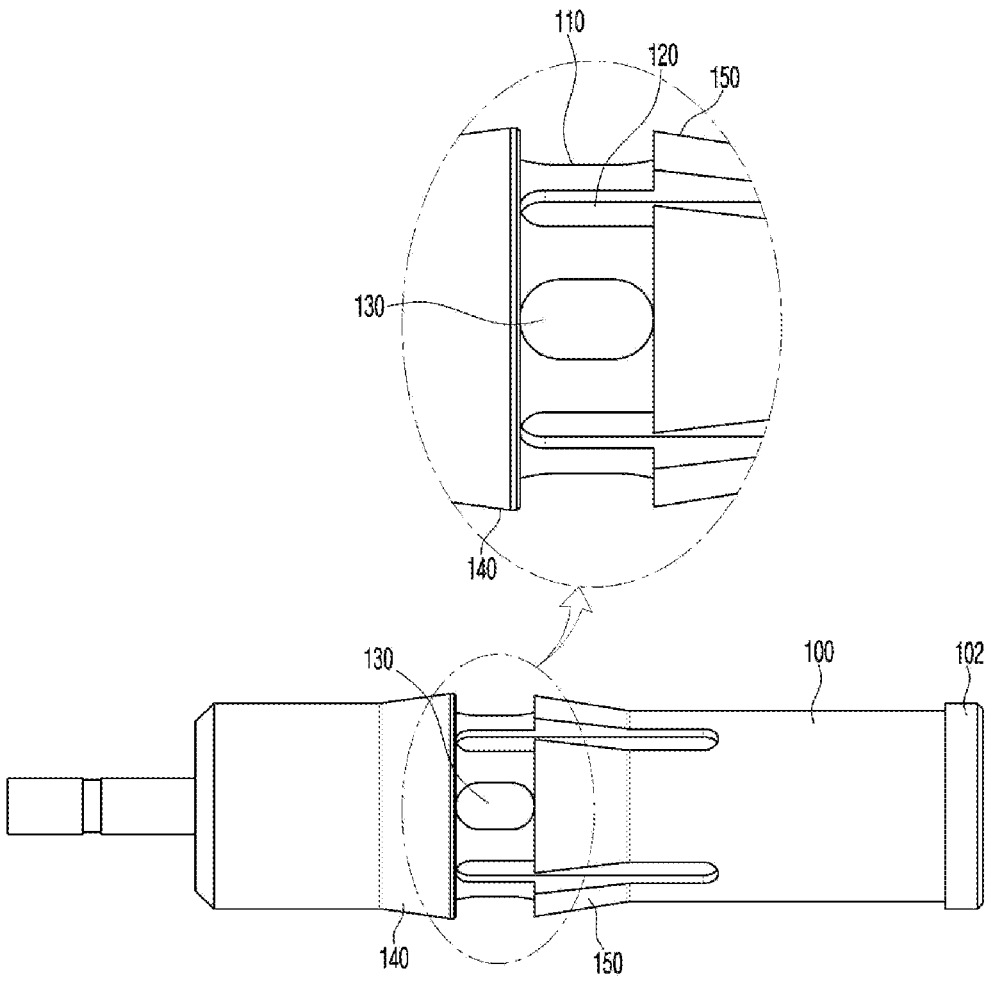
FIG. 3 is a front view showing a holder body according to an embodiment of the present invention.
Figure 4:
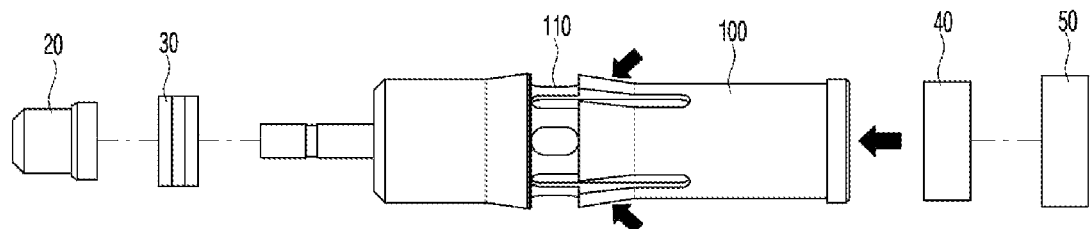
FIG. 4 is an exploded front view showing the ampoule and the ampoule-fixing holder according to the embodiment of the present invention.
Figure 5:
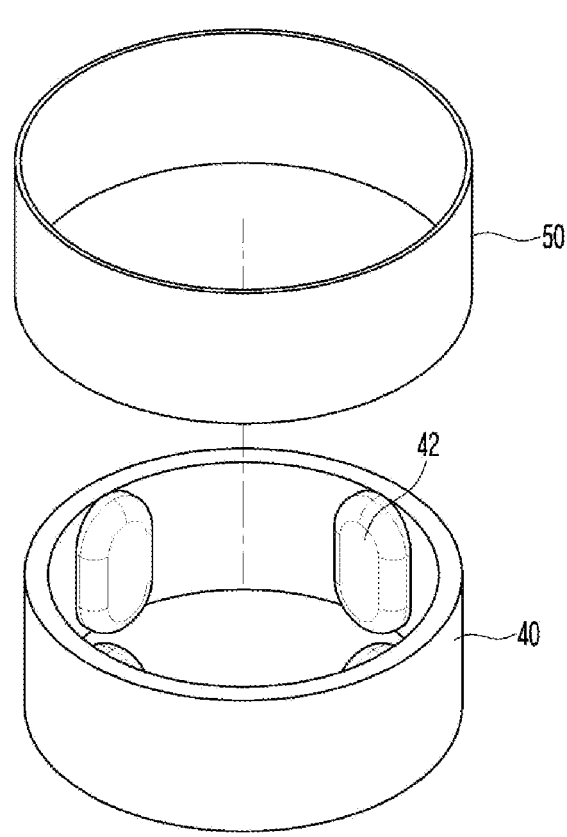
FIG. 5 is a perspective view showing a fixing member according to an embodiment of the present invention.

FIG. 3 is a front view showing the holder body according to the embodiment of the present invention, FIG. 4 is an exploded front view of the ampoule-fixing holder according to the embodiment of the present invention, and FIG. 5 is a perspective view showing the fixing member according to the embodiment of the present invention.

The holder body 100 includes a mounting groove 110 formed in the middle portion thereof to a predetermined depth, in which the elastic rubber ring 40 as the fixing member is mounted. The fixing member 40 is first fitted on the open portion 102 formed at the rear end of the holder body 100 and then is shifted to be fitted into the mounting groove 110. The mounting groove 110 may be formed to have a width corresponding to the width of the fixing member 40 so that the fixing member 40 is tightly fitted in the mounting groove 110.

In addition, the holder body 100 includes a plurality of slits 120 formed therein in the longitudinal direction of the holder body 100 about the central axis of the holder body 100. The slits 120 are disposed so as to be spaced apart from each other at regular intervals in the circumferential direction of the holder body 100. Each of the slits 120 extends from a certain point behind the mounting groove 110 by a predetermined length so as to cross the mounting groove 110.

In addition, the holder body 100 includes a first slanted portion 140 and a second slanted portion 150, which are formed in front of and behind the mounting groove 110, respectively. Each of the first and second slanted portions 140 and 150 gradually increases in thickness toward the mounting groove 110 so as to have a larger outer diameter than the holder body 100.

Since the first slanted portion 140 is formed in front of the mounting groove 110 and the second slanted portion 150 is formed behind the mounting groove 110, the mounting groove 110 is formed to a predetermined depth between the first slanted portion 140 and the second slanted portion 150, and accordingly, the elastic rubber ring 40 as the fixing member is capable of being inserted into the mounting groove 110.

Since the holder body 100 is formed in a cylindrical shape to allow the ampoule 10 to be inserted thereinto, there is a limitation on the extent to which the thickness of the outer wall of the holder body 100 is increased. Therefore, the mounting groove 110 formed in the holder body 100 may not have a sufficient depth. Due to such an insufficient depth of the mounting groove 110, the fixing member 40 may not be tightly fitted into the mounting groove 110.

In order to solve this problem, as described above, the mounting groove 110 of the present invention is defined between the first slanted portion 140 and the second slanted portion 150, which are formed in front of and behind the mounting groove 110, respectively, and include slanted surfaces that gradually increase in thickness toward the mounting groove 110. Accordingly, the mounting groove 110 may have a depth large enough for the fixing member 40 to be tightly fitted therein. Further, the holder body 100 is capable of elastically contracting due to the slits 120, thereby making it possible for the fixing member 40 to be fitted into the mounting groove 110.

In this case, the slits 120 may be formed in the holder body 100 in the longitudinal direction of the holder body 100 so as to cross the second slanted portion 150 and the mounting groove 110.

As shown in FIG. 4, due to the slits 120 formed in the longitudinal direction of the holder body 100 so as to cross the second slanted portion 150 and the mounting groove 110, the holder body 100 elastically contracts in the circumferential direction thereof when the elastic rubber ring 40 is fitted on the open portion 102 of the holder body 100, whereby the elastic rubber ring 40 is capable of passing by the second slanted portion 150, which has a larger outer diameter than the holder body 100, and capable of being fitted into the mounting groove 110.

Furthermore, since the elastic rubber ring 40 is made of an elastically stretchable material, the elastic rubber ring 40 may easily pass by the second slanted portion 150 having a larger outer diameter than the holder body 100, and may be fitted into the mounting groove 110 after passing by the second slanted portion 150.

In addition, the fixing member 40 includes a protruding portion 42 formed on the inner surface thereof. The protruding portion 42 has a predetermined height so as to come into contact with the surface of the ampoule 10, thereby transmitting rotational force to the ampoule 10 when the holder body 100 is rotated. The mounting groove 110 includes an insertion hole 130 formed therein, through which the protruding portion 42 passes to come into contact with the surface of the ampoule 10.

As shown in FIG. 3, it is preferable for the insertion hole 130 to be rounded and elliptical in shape, and it is preferable for the protruding portion 42 to have a lower surface having an elliptical shape corresponding to the shape of the insertion hole 130 and a side surface having a smoothly rounded shape in order to easily pass through the insertion hole 130.

As shown in FIG. 5, a plurality of, preferably four, protruding portions 42 and a plurality of, preferably four, insertion holes 130 may be formed. The plurality of protruding portions 42 may be spaced apart from each other at regular intervals, and the plurality of insertion holes 130 may be spaced apart from each other at regular intervals. In this case, the slits 120 and the insertion holes 130 may alternately be formed in the outer circumferential surface of the holder body 100.

In addition, a fixing-member holder 50 may be fitted on the outer surface of the fixing member 40 in order to hold the fixing member 40 mounted in the mounting groove 110 in the holder body 100.

In order to stably maintain a mounted state of the fixing member 40 in the mounting groove 110 in the holder body 100, it is preferable for the fixing-member holder 50 to be formed in a shape of a ring having an inner diameter identical to the outer diameter of the fixing member 40 and to be made of a material having little or no elasticity.

Figure 6:
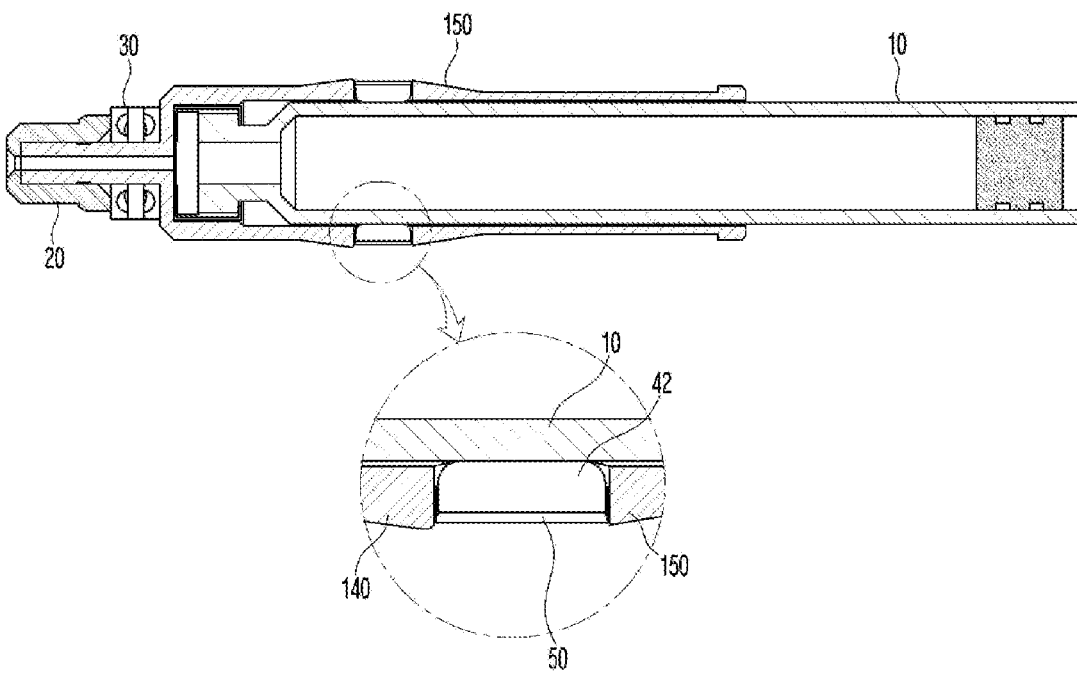
FIG. 6 is a cross-sectional view taken along line A-A in FIG. 1.
Figure 7:
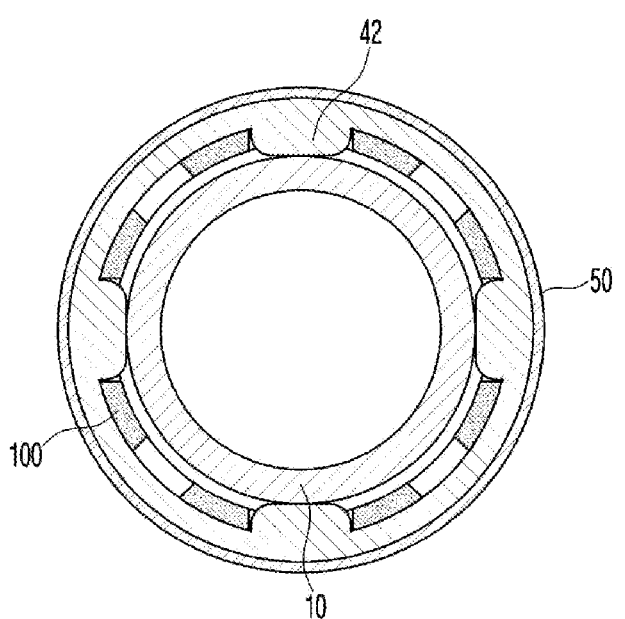
FIG. 7 is a cross-sectional view taken along line B-B in FIG. 1.

FIG. 6 is a cross-sectional view taken along line A-A in FIG. 1, and FIG. 7 is a cross-sectional view taken along line B-B in FIG. 1. FIGS. 6 and 7 illustrate a mounted state of the fixing member 40 in the mounting groove 110 in the holder body 100.

When the fixing member 40 is mounted in the mounting groove 110 in the holder body 100, the protruding portions 42 formed on the inner surface of the fixing member 40 come into contact with the surface of the ampoule 10 through the insertion holes 130 in the mounting groove 110, thereby fixing the ampoule 10 and transmitting rotational force to the ampoule 10 when the holder body 100 is rotated.

According to the present invention, since the protruding portions 42 of the fixing member 40 hold the ampoule 10, the ampoule 10 may be stably fixed, and accordingly, power of a motor may be effectively transmitted to the ampoule 10 without rotational slippage. In addition, it may be possible to cope with variation in outer diameter of ampoules and thus to prevent variation in fixing force caused by variation in outer diameter of ampoules.

Further, since the fixing member 40 made of rubber is fitted on the holder body 100 to fix the ampoule 10, the ampoule-fixing holder according to the present invention may be continuously used merely by replacing the fixing member 40, and may prevent reduction in fixing force due to deformation thereof over time.

Figure 8:
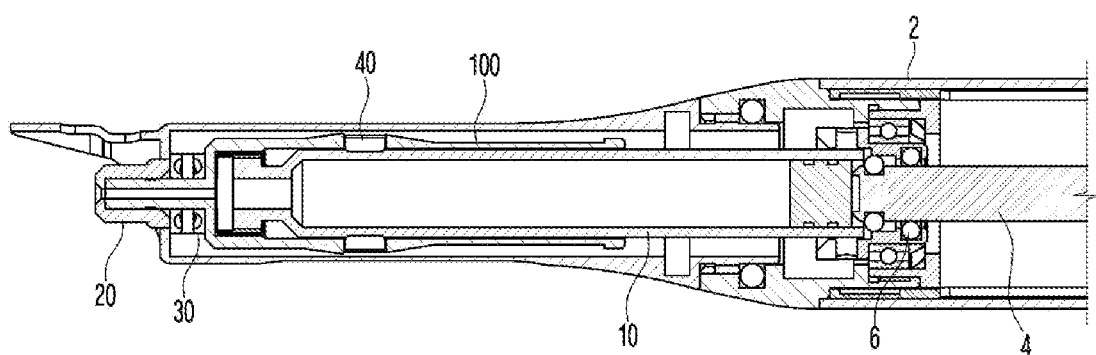
FIG. 8 is a cross-sectional view showing an anesthetic solution injection device including the ampoule-fixing holder according to an embodiment of the present invention.

FIG. 8 is a cross-sectional view showing an anesthetic solution injection device including the ampoule-fixing holder according to an embodiment of the present invention. The anesthetic solution injection device according to the embodiment of the present invention includes an ampoule 10 containing an anesthetic solution, the above-described ampoule-fixing holder configured to fix the ampoule 10, an injection needle (not shown) mounted to one end of the ampoule-fixing holder, and a handpiece 2 including a pusher 4 inserted into the other end of the ampoule-fixing holder to push and fix the ampoule 10 inserted into the ampoule-fixing holder and a spring 6 configured to push the ampoule-fixing holder mounted in the handpiece 2 using resilient force thereof at the other end of the ampoule-fixing holder.

The handpiece 2 is an instrument configured to apply pressure to the ampoule 10 fixed to the ampoule-fixing holder. The handpiece 2 may include a motor configured to generate pressure to eject the anesthetic solution through the injection needle, a user input unit configured to allow a user to input a command for control of operation of the handpiece 2, a controller configured to control the motor in response to the command received from the user input unit, and a battery configured to supply power to the user input unit.

The above-described components of the handpiece 2, i.e. the motor, the user input unit, the controller, and the battery, may be implemented using well-known technology. For example, the user input unit may be mounted on the outer surface of the handpiece 2, and may include a power on/off button, an anesthetic solution injection amount control button, and a bubble removal command button in order to control the amount of anesthetic solution to be injected and to control operation of the handpiece 2.

Further, since a built-in battery is mounted in the handpiece 2, it may be possible to supply power to the motor, the user input unit, and the controller without a separate external power supply cable. Accordingly, the anesthetic solution injection device according to the present invention may exhibit excellent portability.

The present invention is characterized by the structure of the ampoule-fixing holder mounted in the handpiece 2, and the motor, the user input unit, the controller, and the battery of the handpiece 2 may be implemented in various configurations. Therefore, a detailed description thereof will be omitted.

As is apparent from the above description, according to the present invention, a fixing member fitted on the outer circumferential surface of a holder body is implemented as an elastic rubber ring, and includes protruding portions formed on the inner surface thereof in order to hold an ampoule, whereby the ampoule may be stably fixed, and accordingly, power of a motor may be effectively transmitted to the ampoule without rotational slippage. Further, manufacturing time and cost may be reduced.

In addition, it may be possible to cope with variation in outer diameter of ampoules and thus to prevent variation in fixing force caused by variation in outer diameter of ampoules. Further, it may be possible to prevent reduction in fixing force due to deformation of an ampoule-fixing holder over time. Furthermore, it may be possible to maintain fixing force only using a structure of pushing the ampoule-fixing holder regardless of the contraction or expansion properties of the material of the ampoule-fixing holder.

Although specific embodiments of the present invention have been disclosed for illustrative purposes, those skilled in the art will appreciate that various modifications, additions, and substitutions are possible, without departing from the scope and spirit of the invention as disclosed in the accompanying claims.

What is claimed is:

1. An ampoule-fixing holder for an intraosseous anesthetic solution injection device, the ampoule-fixing holder comprising:

a cylindrical holder body comprising an open portion formed at a rear end thereof to allow an ampoule containing an anesthetic solution to be inserted thereinto or removed therefrom;

a head configured to enable mounting of an injection needle to a front end of the holder body;

a rotary body disposed between the head and the holder body to withstand rotational force and an axial load; and a fixing member configured to firmly hold the ampoule inserted into the holder body to effectively transmit rotational force to the ampoule, wherein the fixing member is implemented as an elastic rubber ring configured to be first fitted on the open portion of the holder body and then shifted to be mounted on an outer circumferential surface of the holder body, wherein the holder body comprises a mounting groove formed in a middle portion thereof to a predetermined depth to allow the elastic rubber ring to be mounted therein and a plurality of slits formed in the holder body in a longitudinal direction of the holder body about a central axis of the holder body, and wherein, when the elastic rubber ring is fitted on the open portion of the holder body, the holder body elastically contracts in a circumferential direction thereof to allow the elastic rubber ring to be fitted into the mounting groove, wherein the fixing member comprises at least one protruding portion formed on an inner surface thereof so as to come into contact with a surface of the ampoule to transmit rotational force to the ampoule when the holder body is rotated, and wherein the mounting groove comprises at least one insertion hole formed therein to allow the at least one protruding portion to pass therethrough and to come into contact with the surface of the ampoule.

2. The ampoule-fixing holder according to claim 1, wherein the at least one protruding portion comprises a plurality of protruding portions disposed so as to be spaced apart from each other at regular intervals, wherein the at least one insertion hole comprises a plurality of insertion holes disposed so as to be spaced apart from each other at regular intervals, and wherein the plurality of slits and the plurality of insertion holes are alternately formed in the outer circumferential surface of the holder body.

3. The ampoule-fixing holder according to claim 1, wherein the holder body comprises a first slanted portion and a second slanted portion formed in front of and behind the mounting groove, respectively, and wherein each of the first slanted portion and the second slanted portion gradually increases in thickness toward the mounting groove so as to have a larger outer diameter than the rest of the holder body.

4. The ampoule-fixing holder according to claim 3, wherein the plurality of slits is formed in the holder body in the longitudinal direction of the holder body so as to cross the second slanted portion and the mounting groove.

5. The ampoule-fixing holder according to claim 1, further comprising a fixing-member holder configured to be fitted on an outer surface of the fixing member in order to hold the fixing member in the mounting groove in the holder body.

6. The ampoule-fixing holder according to claim 1, wherein the head is bonded to a front portion of the holder body using an adhesive.

7. An anesthetic solution injection device comprising:

an ampoule containing an anesthetic solution;

the ampoule-fixing holder described in claim 1, the ampoule-fixing holder being configured to fix the ampoule;

an injection needle mounted to one end of the ampoule-fixing holder; and a handpiece comprising a pusher inserted into an opposite end of the ampoule-fixing holder to push and fix the ampoule inserted into the ampoule-fixing holder and a spring configured to push the ampoule-fixing holder mounted in the handpiece using resilient force at the opposite end of the ampoule-fixing holder.

8. The anesthetic solution injection device according to claim 7, wherein the handpiece comprises:

a motor configured to generate pressure to eject the anesthetic solution through the injection needle;

a user input unit configured to allow a user to input a command for control of operation of the handpiece;

a controller configured to control the motor in response to the command received from the user input unit; and a battery configured to supply power to the user input unit.

\* \* \* \* \*